United States Patent [19]

Bauer

[11] Patent Number: 5,218,644
[45] Date of Patent: Jun. 8, 1993

[54] DEVICE FOR RECOGNIZING LATENT INFORMATION

[76] Inventor: Eric Bauer, Rue Maujobia 113, 2006 Neuchatel Canton of Neuchâtel, Switzerland

[21] Appl. No.: 673,012

[22] Filed: Mar. 21, 1991

[30] Foreign Application Priority Data

Mar. 28, 1990 [CH] Switzerland ............... 1026/90

[51] Int. Cl.⁵ ................................. G06K 9/00
[52] U.S. Cl. ................................ 382/4; 382/2; 73/644; 310/335
[58] Field of Search ........... 382/4, 5, 2; 73/644; 310/335; 356/71; 359/2; 340/825.31, 825.34

[56] References Cited

U.S. PATENT DOCUMENTS

| | | | |
|---|---|---|---|
| 3,947,128 | 3/1976 | Weinberger et al. | 356/71 |
| 4,120,585 | 10/1978 | DePalma et al. | 356/71 |
| 4,414,684 | 11/1983 | Blonder | 382/4 |
| 4,777,958 | 10/1988 | Ophir | 128/660.01 |
| 4,972,476 | 11/1990 | Nathans | 380/23 |
| 4,977,601 | 12/1990 | Bicz | 382/4 |

OTHER PUBLICATIONS

Follette et al., "Direct Optical Input System for Fingerprint Verification", *IBM Technical Disclosure Bulletin*, vol. 16, No. 11, Apr. 1974, pp. 3572-3573.

*Primary Examiner*—Leo H. Boudreau
*Assistant Examiner*—Andrew W. Johns
*Attorney, Agent, or Firm*—Silverman, Cass & Singer, Ltd.

[57] ABSTRACT

A device for recognizing latent information including an asymmetrical reading head in the form of a truncated cone which is inclined (oblique). The image of the latent information furnished by the reading head is deformed or "warped" with respect to the image which would be furnished by a perfectly symmetrical reading head (a right truncated cone). Hence, different categories of users of an installation can be provided with device having different reading heads furnishing each user with a proper image for the information he is permitted to access so as to prevent access to non-permitted information, each category of users having access to a part of the information corresponding to the specific image furnished by the proper reading head of his device.

17 Claims, 2 Drawing Sheets the
DEVICE FOR RECOGNIZING LATENT INFORMATION

BACKGROUND OF THE INVENTION a) Field of the Invention

The present invention relates to a method of using a device for reading latent complex information, especially biometric information, and to the device for carrying out said method.

The reading of latent complex information, especially biometric information, gives rise to problems which have prompted solutions which are not entirely satisfactory.

b) Description of the Prior Art

One of the drawbacks of the known methods lies in the fact that all of the users of the installations, for reading of information of a same type, receive the same "image", and this can permit access to information intended not to be disclosed to certain users. As a matter of fact, once a user is in possession of the accessed information made, it is possible for the user to have access to stocks of data related to the information, data that might be intended to be keep confidential, or to be put only partially at disposal, of specified people or groups of people. In other words, with the known methods, it is possible for users to effect cross-checks of information which it may be desired to prevent. Thus, for instance, it may be desired to restrict access to data relating to a specific group of people to which only parts of the data are useful.

SUMMARY OF THE INVENTION

The object of the invention is to remove the above disadvantage by providing a device which permits users entitled to have access to a part of data only not to have access to the rest of the data.

This object is achieved in accordance with the invention due to the fact that a user produces, by means of a device for rendering apparent a latent complex information, an alteration of at least a part of the information which is made apparent so as to produce several non identical images of the latent information.

The object of the invention is also achieved in accordance with the invention due to the fact that the device for carrying out the method comprises structure for rendering apparent a latent complex information, at least a part of said device being arranged in such a way as to produce an altered image of the information.

The various features of the invention will be apparent from the following description, drawings and claims, the scope of the invention not being limited to the drawings themselves as the drawings are only for the purpose of illustrating ways in which the principles of the invention can be applied. Other embodiments of the invention utilising the same or equivalent principles may be used and structural changes may be made as desired by those skilled in the art without departing from the present invention and the purview of the appended claims.

Figure 1:
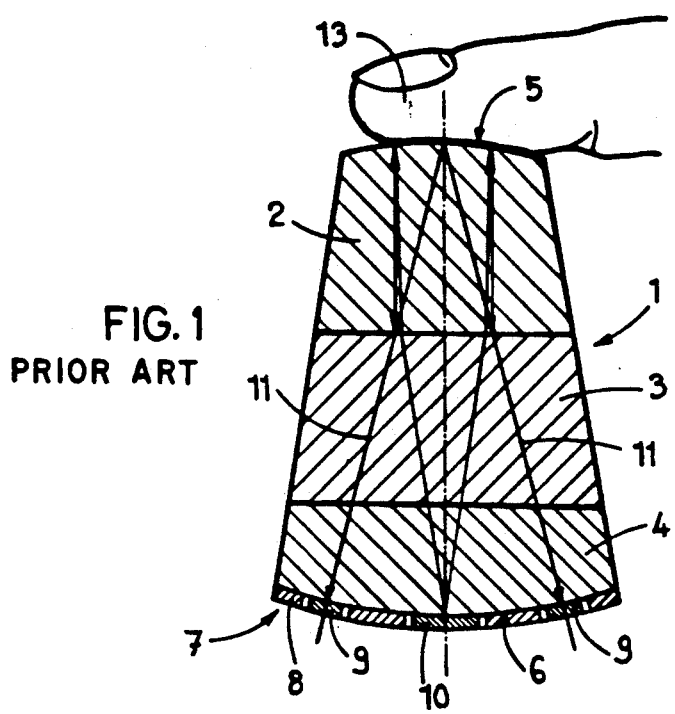
FIG. 1 is a diagrammatic sectional view of a known reading head, belonging to the prior art, permitting the reading of latent information.

The conventional reading head represented in FIG. 1, generally designated by reference 1, comprises a composite body of frusto-conical shape, constituted by three parts 2, 3 and 4, the two first ones made of two different plastic materials and the third one made of an active material, for instance of a piezo-ceramic.

The two axial faces of head 1, designated by references 5 and 6, are both convex. The face 6 is covered with a plate of resonance, generally designated by reference 7, made of a dielectric mass 8, in which are embedded metallized studs 9 and 10 which constitute, with the dielectric mass, a capacity.

Such a reading head being known per se, as well as its operating mode, it will not be disclosed in more detail. It is sufficient to explain that one of the metallized studs, i.e. central stud 10, is submitted to the action of a generator of ultrasounds and that the waves it emits are reflected by the finger, designated by reference 13, of the person the identity of which is to be checked, placed on the front face 5 of the head, and sent on and by the several studs 9 and 10 which, by interaction, produce finally a signal-image of the biometric information contained by the finger 13.

If such a reading head, cooperating with a suitable electronic, is used for instance for checking the finger such as the finger indicted at 13 in FIG. 1, in contact with the convex face 5 of the reading head, the ultrasounds which are reflected by this finger give signals which, owing to a suitable electronic, can be transformed into a displayed image constituting a biometric image which is different from one person to another.

Figure 2:
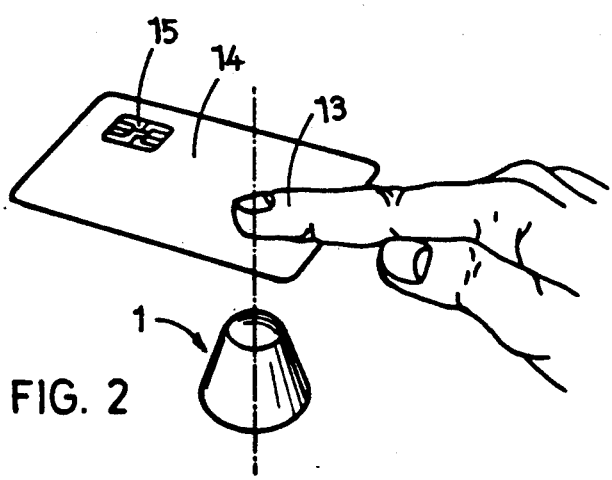
FIG. 2 shows a mode of utilization of this reading head.

Thus, one can check the finger of the carrier of a data processing card such as card 14 of FIG. 2, provided with a microprocessor 15, which contains coded information corresponding to the biometric information given by the carrier of the card. Any misuse of the card will be prevented this way since it is necessary, in order for the card to operate, that the coded information it contains corresponds to the latent information carried by the finger of the carrier and which is read by the reading head.

Figure 3:
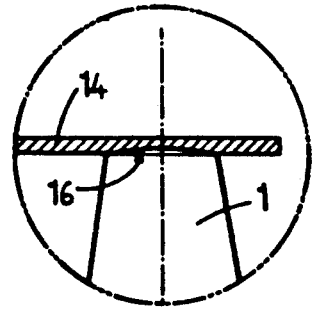
FIG. 3 is a sectional view of a detail of the said reading head and of a data processing card used with said reading head.

As can be seen from FIG. 3, the data processing card 14 includes a concave circular area 16 on the surface opposite that which the user of the card places his finger. The end of the reading head 1 is engaged in the area 16.

Figure 4:
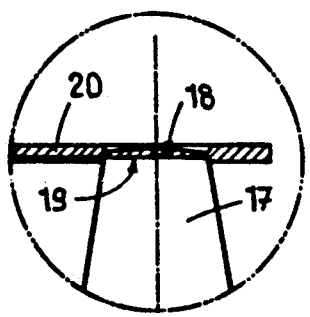
FIGS. 4 and 5 are sectional views similar to that of FIG. 3 illustrating modifications of the data processing card and of the corresponding reading head.

In the modification of FIG. 4, the reading head, designated by reference 17, has an extremity, designated by 18, which is planar, and which engages a recessed portion 19 of the data processing card, designated by reference 20, formed on the side opposite which the user of the card places the end of his finger.

Figure 5:
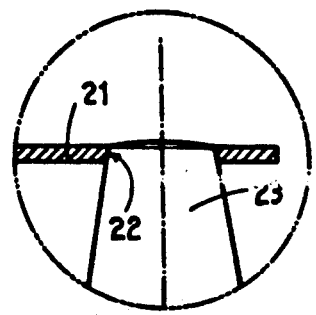

In the modification of FIG. 5, a data processing card 21 is provided with a trasversing aperture 22 in which engages the end of the reading head, designated by reference 23.

According to the known arrangements, the reading head, which is frusto-conical, is symmetrical with respect to its longitudinal axis.

DESCRIPTION OF THE PREFERRED EMBODIMENTS

Figure 6:
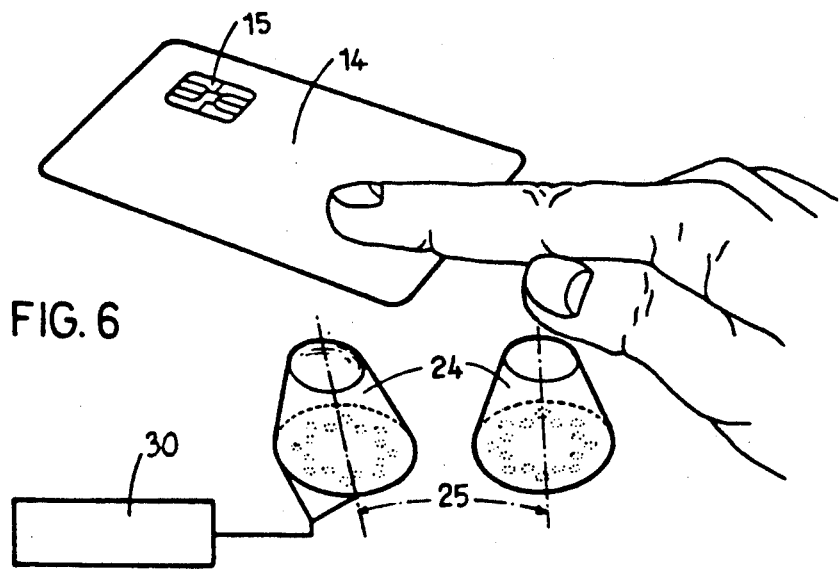
FIG. 6 is a diagrammatic perspective view of a first embodiment of a reading head of a latent information reading installation according to the present invention.

According to the first embodiment of the invention, shown in FIG. 6, a reading head, designated by reference 24, is asymmetrical with respect to its longitudinal axis, designated by reference 25. Hence, the information made apparent by means of reading head 24, from a latent information, is altered or distorted, the image of the apparent information being different from that which would be obtained by means of a conventional reading head such as that of FIG. 1, for instance.

The information from reading head 24 is transformed by electronic device 30 into information suitable for display.

Thus, several categories of users of a bank of data, for example, insurance companies and government agencies, can be equipped with reading installations provided with different reading heads.

Each category of user will have its own reading head which is different for each category of user, with the result that the desired distortion of the recepted image will be different for each category of user. Each distorted image will give access to a selected portion of the data contained in the bank. Thus, the insurance company user will have access only to information data relating thereto, even though the access is obtained at a government agency installation. In other words, a single data bank is usable for one group of people without that group having access to certain other information in the same data bank.

Figures 7A, 7B, 7C:
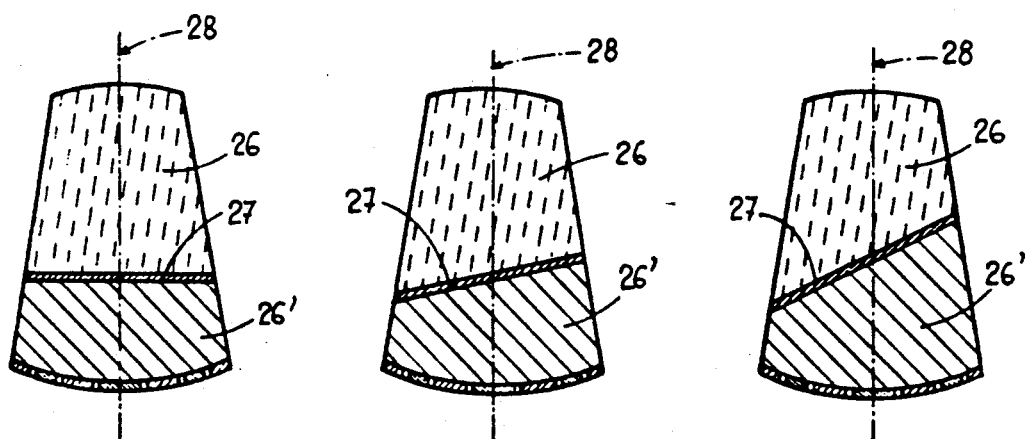
FIG. 7A, B, C are sectional views of a first modification of reading heads.

The desired result is achieved by employing reading heads 24 which differ in their diffraction characteristic by the geometry of the diffraction plate 27. FIGS. 7A, B, C show reading heads where the inclination of the diffraction plate with respect to the longitudinal axis 28 of varied. Diffraction plate 27 separates the two different plastic materials 26, 26' which form the body of the reading head.

One could also act by the choice of the materials constituting the body of the reading head and by the number of these materials or of the diffraction plates of a same head, thus producing different diffracting effects.

In the above mentioned examples, the object aimed—to deform the information which is made apparent—is obtained by diffraction.

However, one could also, with a same object, use other means.

Figure 8:
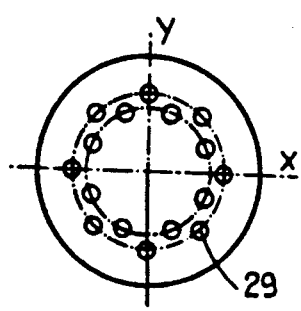
FIGS. 8 and 9 are bottom plan views showing a second modification of reading heads.
Figure 9:
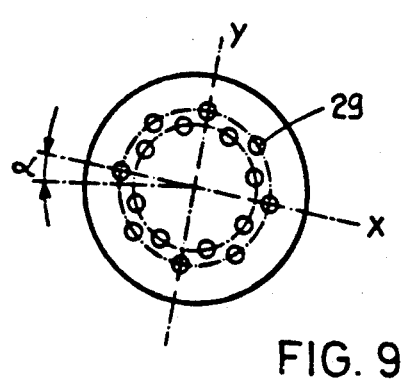

Thus, one could modify the angular orientation, with respect to the longitudinal axis of the reading head, of the plate of resonance of the head. It is necessary, so that this be efficient, that the metallized studs designated by reference 29 in FIGS. 8 and 9 are not disposed symmetrically with respect to the center of the plate of resonance. In this case, an angular adjustment of the plate, indicated by the angle α of FIG. 9, "warps" the given information.

The metallized studs 29 in FIGS. 8 and 9 comprise emitting and receiving members and the position of these members vary from head to head. Accordingly, the construction of such reading head different and operate to produce nonidentical, distorted images of information.

One could also act on the electronic means which uses the signals furnished by the reading head to render them displayable for producing a warped or modified image of the received information.

I claim:

1. A device for recognizing information from a person's finger comprising, means to produce a plurality of non-identical distorted images of the information, said images being produced by diffraction, said means to produce the image including a plurality of reading heads, each of said heads including detection plates provided with emitting and receiving members, the position of said emitting and receiving members being different for each of said heads.

2. A device as claimed in claim 1, in which said non-identical images are in the form of ultrasounds.

3. A device as claimed in claim 2 in which the geometry of each of the reading heads is different.

4. A device as claimed in claim 2 in which said means to produce the images comprise a plurality of reading heads which heads include a diffraction plate, the position of the diffraction plate of each said heads being different.

5. A device as claimed in claim 2 in which said means to produce the images comprise reading heads having a body, the material from which the body of each of the heads is made being different.

6. A device as claimed in claim 1 in which said means to produce the images are reading heads for producing ultrasounds, at least portions of each of said reading heads being formed so as to produce a differently altered image of said information.

7. A device as claimed in claim 6 in which the geometry of each of the reading heads is different.

8. A device as claimed in claim 6 in which said means to produce the images comprise a plurality of reading heads which heads include a diffraction plate, the position of the diffraction plate of each of said heads being different.

9. A device as claimed in claim 6 in which said means to produce the images comprise reading heads having a body, the material from which the body of each of the heads is made being different.

10. A device as claimed in claim 6 in which said means to produce the images comprise reading heads which include detection plates provided with emitting and receiving members, the position of said emitting and receiving members being different for each of said reading heads.

11. A device as claimed in claim 6 in which said means to produce the images comprise reading heads which produce signals, and electronic means for transforming said signals into information for display.

12. A device as claimed in claim 1 in which the geometry of each of the reading heads is different.

13. A device as claimed in claim 1 in which the position of the diffraction plate of each of said heads differs with respect to the longitudinal axis of said heads.

14. A device as claimed in claim 1 in which each of said reading heads comprises a body of different materials from which the body of each of the heads is made.

15. A device as claimed in claim 14 in which said body is made of composite materials.

16. A device as claimed in claim 1 in which each of said reading heads produces signals, and electronic means for transforming said signals into displayable information.

17. A device for recognizing information from a person's finger comprising, means to produce a plurality of non-identical distorted images of the information, said images being produced by diffraction, said means to produce the images including reading heads for producing ultrasounds, at least portions of said heads being formed so as to produce an altered image of said information, said reading heads including detection plates provided with emitting and receiving members, the position of said emitting and receiving members being different for each of said heads.

* * * * *